(12) United States Patent
Mostafavi et al.

(10) Patent No.: US 9,153,034 B2
(45) Date of Patent: Oct. 6, 2015

(54) IMAGE PROCESSING OF IMAGES THAT INCLUDE MARKER IMAGES

(71) Applicant: Varian Medical Systems, Inc., Palo Alto, CA (US)

(72) Inventors: Hassan Mostafavi, Los Altos, CA (US); Andrew Jeung, Mountain View, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 149 days.

(21) Appl. No.: 14/040,599

(22) Filed: Sep. 27, 2013

(65) Prior Publication Data

US 2014/0270365 A1    Sep. 18, 2014

Related U.S. Application Data

(60) Provisional application No. 61/798,546, filed on Mar. 15, 2013.

(51) Int. Cl.
*G06K 9/00* (2006.01)
*G06T 7/20* (2006.01)
*A61B 6/00* (2006.01)
(Continued)

(52) U.S. Cl.
CPC ............... *G06T 7/2033* (2013.01); *A61B 6/52* (2013.01); *A61N 5/1049* (2013.01); *G06T 7/0048* (2013.01); *G06T 2207/10116* (2013.01); *G06T 2207/20021* (2013.01); *G06T 2207/30061* (2013.01); *G06T 2207/30096* (2013.01)

(58) Field of Classification Search
USPC ......... 382/100, 103, 106–107, 128–134, 162, 382/168, 173, 181, 199, 219, 232, 254, 274, 382/276, 286–294, 305, 312; 358/518; 378/4, 21, 65; 600/427
See application file for complete search history.

(56) References Cited

U.S. PATENT DOCUMENTS

2005/0059887 A1*  3/2005  Mostafavi et al. ............ 600/427
2005/0200921 A1*  9/2005  Yuan et al. .................... 358/518
(Continued)

OTHER PUBLICATIONS

International Search Report and the Written Opinion dated Jul. 18, 2014 for related PCT Patent Application No. PCT/US14/18764, 11 pages.

(Continued)

*Primary Examiner* — Seyed Azarian
(74) *Attorney, Agent, or Firm* — Vista IP Law Group, LLP (57) ABSTRACT

An image processing method, includes: obtaining an image, the image having marker images and a background image; identifying presence of an object in the background image using a processor; and providing a signal for stopping a procedure if the presence of the object is identified. An image processing apparatus, includes: a processor configured for: obtaining an image, the image having marker images and a background image; identifying presence of an object in the background image; and providing a signal for stopping a procedure if the presence of the object is identified. A computer product having a non-transitory medium storing a set of instructions, an execution of which causes an image processing method to be performed, the method includes: obtaining an image, the image having marker images and a background image; identifying presence of an object in the background image; and providing a signal for stopping a procedure if the presence of the object is identified.

21 Claims, 7 Drawing Sheets

(51) Int. Cl.
*A61N 5/10* (2006.01)
*G06T 7/00* (2006.01)
*A61B 5/05* (2006.01)

(56) References Cited

U.S. PATENT DOCUMENTS

2006/0245628 A1* 11/2006 Jeung et al. .................. 382/128
2010/0080354 A1* 4/2010 Fu et al. ......................... 378/65
2011/0123070 A1* 5/2011 Sebok ........................... 382/106
2011/0135176 A1* 6/2011 Lendl ............................ 382/130

OTHER PUBLICATIONS

Keller, et al., "Active Pedestrian Safety by Automatic Braking and Evasive Steering", IEEE Transactions on Intelligent Transportation Systems, vol. 12, No. 4, Dec. 2011, 12 pages.

Maji, et al., "Part of Image Tagging Statistical NLP Final Project", Department of Computer Science and Engineering University of California, Berkeley, Spring 2008, 4 pages.

Bhat, et al., "Fourier Analysis of the 2D Screened Poisson Equation for Gradient Domain Problems", 2008, 14 pages.

* cited by examiner

IMAGE PROCESSING OF IMAGES THAT INCLUDE MARKER IMAGES

RELATED APPLICATION DATA

This application claims priority to and the benefit of U.S. Provisional Patent Application No. 61/798,546, filed on Mar. 15, 2013, the entire disclosure of which is expressly incorporated by reference herein.

FIELD

An embodiment described herein relates to image processing, and more specifically, to method and system for processing images that include marker images.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. In certain types of radiotherapy, the irradiation volume can be restricted to the size and shape of the tumor or targeted tissue region to avoid inflicting unnecessary radiation damage to healthy tissue. For example, conformal therapy is a radiotherapy technique that is often employed to optimize dose distribution by conforming the treatment volume more closely to the targeted tumor.

Normal physiological movement represents a limitation in the clinical planning and delivery of conventional radiotherapy and conformal therapy. Normal physiological movement, such as respiration or heart movement, can cause a positional movement of the tumor or tissue region undergoing irradiation. If the radiation beam has been shaped to conform the treatment volume to the exact dimensions of a tumor, then movement of that tumor during treatment could result in the radiation beam not being sufficiently sized or shaped to fully cover the targeted tumoral tissue.

To address this problem, physiological gating of the radiation beam during treatment may be performed, with the gating signal synchronized to the movement of the patient's body. In this approach, instruments are utilized to measure the physiological state of the patient with reference to the particular physiological movement being examined. For example, respiration has been shown to cause movements in the position of a lung tumor in a patient's body. If radiotherapy is being applied to the lung tumor, then a position sensor can be attached to the patient to measure the patient's respiration cycle. The radiation beam can be gated based upon certain threshold points within the measured respiratory cycle, such that the radiation beam is disengaged during periods in the respiration cycle that correspond to excessive movement of the lung tumor.

One type of position sensor that may be used in medical gating is a camera system that includes a camera configured to sense markers on a marker block that is attached to the patient. During use, the camera is configured to determine the position of the marker block (which corresponds with the patient's physiological motion, such as breathing) based on marker images captured by the camera. In some cases, it may be desirable to ensure that only the marker images (i.e., not images of other objects) be used to determine the position of the marker block. Otherwise, the resulting position determined may not be the correct position of the marker block.

As such, Applicant of the subject application believes that a new method and system for processing images captured by a marker system camera may be desirable.

SUMMARY

An image processing method, includes: obtaining an image, the image having marker images and a background image; identifying presence of an object in the background image using a processor; and providing a signal for stopping a procedure if the presence of the object is identified.

Optionally, the act of identifying the presence of the object in the background comprises: dividing the image into a plurality of image portions arranged in a matrix; and determines a mean or median value of pixel values in each of the image portions.

Optionally, the act of identifying the presence of the object in the background further comprises determining a histogram using the determined mean or median values.

Optionally, the act of identifying the presence of the object further comprises determining if any of the mean or median values exceeds a peak value of the histogram by more than a specified threshold.

Optionally, the method further includes setting a size for one or more of the image portions.

Optionally, the size is set manually.

Optionally, the size is set automatically using the processor.

Optionally, the method further includes flattening the image in greyscale so that gradient variation across the image is reduced.

Optionally, the act of flattening the image in greyscale comprises: sampling a set of points in the image; generating an uniform gradient image with uniform grayscale gradient which is the best-fit to the sampled set of points; and subtracting the uniform gradient image from the received image to generate an output image.

Optionally, the method further includes excluding the object as a marker.

Optionally, the act of receiving an image comprises receiving a sequence of images that includes the image, and the act of identifying the presence of the object is performed on a subset of the sequence of images.

An image processing apparatus, includes: a processor configured for: obtaining an image, the image having marker images and a background image; identifying presence of an object in the background image; and providing a signal for stopping a procedure if the presence of the object is identified.

Optionally, the processor is configured for: dividing the image into a plurality of image portions arranged in a matrix; and determines a mean or median value of pixel values in each of the image portions.

Optionally, the processor is configured for determining a histogram using the determined mean or median values.

Optionally, the processor is configured for determining if any of the mean or median values exceeds a peak value of the histogram by more than a specified threshold.

Optionally, the processor is configured to obtain a size for one or more of the image portions.

Optionally, the processor is configured to obtain the size by receiving an input from a user that represents the size.

Optionally, the processor is configured to obtain the size by determining the size using an algorithm.

Optionally, the processor is further configured for flattening the image in greyscale so that gradient variation across the image is reduced.

Optionally, the processor is configured to perform the act of flattening the image in greyscale by: sampling a set of points in the image; generating an uniform gradient image with uniform grayscale gradient which is the best-fit to the sampled set of points; and subtracting the uniform gradient image from the received image to generate an output image.

Optionally, the processor is further configured to exclude the object as a marker.

Optionally, the processor is configured to receive a sequence of images that includes the image, and the processor is configured to perform the act of identifying the presence of the object on a subset of the sequence of images.

A computer product having a non-transitory medium storing a set of instructions, an execution of which causes an image processing method to be performed, the method includes: obtaining an image, the image having marker images and a background image; identifying presence of an object in the background image; and providing a signal for stopping a procedure if the presence of the object is identified.

Other and further aspects and features will be evident from reading the following detailed description.

BRIEF DESCRIPTION OF THE DRAWINGS

The drawings illustrate the design and utility of various features described herein, in which similar elements are referred to by common reference numerals. These drawings are not necessarily drawn to scale. In order to better appreciate how the above-recited and other advantages and objects are obtained, a more particular description will be rendered, which are illustrated in the accompanying drawings. These drawings depict only exemplary features and are not therefore to be considered limiting in the scope of the claims.

DETAILED DESCRIPTION

Various features are described hereinafter with reference to the figures. It should be noted that the figures are not drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated.

Radiation System

Figure 1:
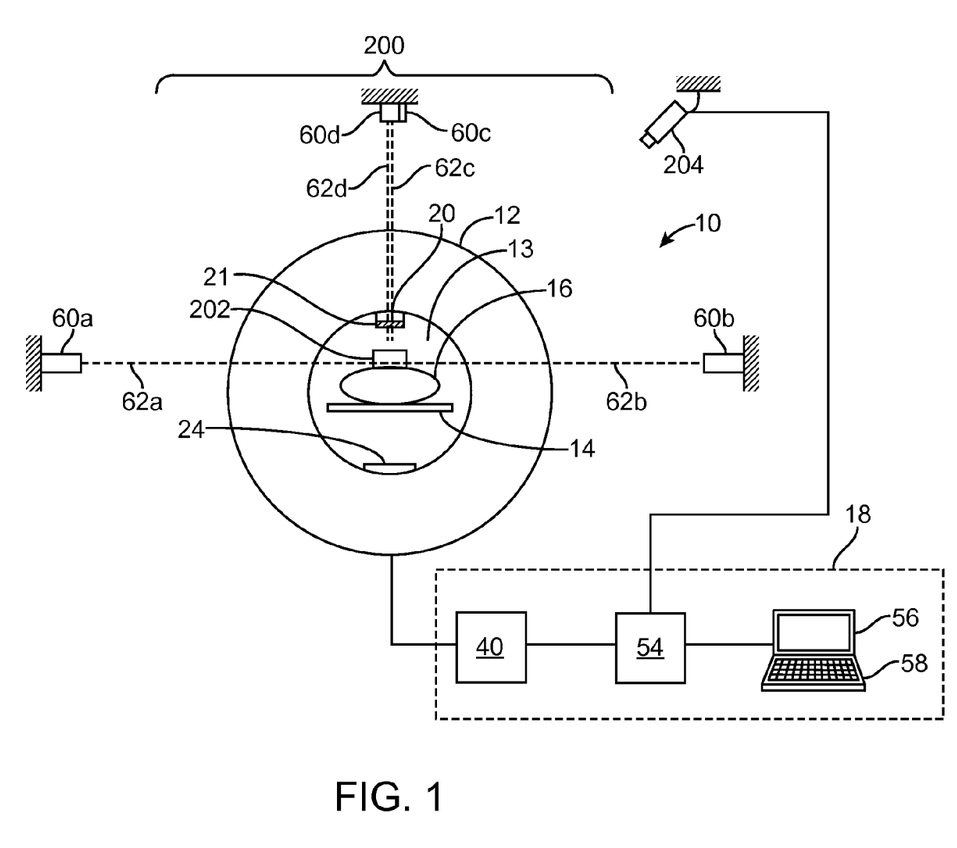
FIG. 1 illustrates a radiation system being used with a marker system.

FIG. 1 illustrates a radiation system 10. The system 10 includes a gantry 12 having an opening (or bore) 13, a patient support 14 for supporting a patient 16, and a control system 18 for controlling an operation of the gantry 12. In the illustrated embodiments, the gantry 12 has a slip-ring configuration (donut shape). Alternatively, the gantry 12 can have other configurations, such as a C-arm configuration. The system 10 also includes a radiation source (e.g., x-ray source) 20 that projects a beam of radiation towards the patient 16, and a collimator 21 for changing a shape of the beam. The system 10 also includes a detector 24 on an opposite side of the gantry 12, which in some cases, may be used to receive radiation exiting from the patient 16, and generate image(s) using the received radiation. The detector 24 has a plurality of sensor elements configured for sensing a x-ray that passes through the patient 16. Each sensor element generates an electrical signal representative of an intensity of the x-ray beam as it passes through the patient 16. In other embodiments, the system 10 does not include the detector 24.

In the illustrated embodiments, the radiation source 20 is a treatment radiation source for providing treatment energy. In other embodiments, the radiation source 20 may be a diagnostic radiation source for providing diagnostic energy (e.g., energy that is suitable for generating an image). In further embodiments, the radiation source 20 can be configured to selectively provide treatment energy and diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV.

The control system 18 includes a processor 54, such as a computer processor, coupled to a source rotation control 40. The control system 18 may also include a monitor 56 for displaying data and an input device 58, such as a keyboard or a mouse, for inputting data. During a scan to acquire x-ray projection data (e.g., cone beam CT image data), the source 20 rotates about the patient 16. The rotation of the source 20 and the operation of the radiation source 20 are controlled by the source rotation control 40, which provides power and timing signals to the radiation source 20 and controls a rotational speed and position of the source 20 based on signals received from the processor 54. Although the control 40 is shown as a separate component from the gantry 12 and the processor 54, in alternative embodiments, the control 40 can be a part of the gantry 12 or the processor 54.

In some embodiments, the system 10 may be a treatment system configured to deliver treatment radiation beam towards the patient 16 at different gantry angles. During a treatment procedure, the source 20 rotates around the patient 16 and delivers treatment radiation beam from different gantry angles towards the patient 16. While the source 20 is at different gantry angles, the collimator 21 is operated to change the shape of the beam to correspond with a shape of the target tissue structure. For example, the collimator 21 may be operated so that the shape of the beam is similar to a cross sectional shape of the target tissue structure. In another example, the collimator 21 may be operated so that different portions of the target tissue structure receive different amount of radiation (as in an IMRT procedure).

In other embodiments, the system 10 may be an imaging system. In such cases, the collimator 21 may not be needed. During a radiation imaging procedure, the radiation source 20 generates and directs an x-ray beam towards the patient 16, while the detector 24 measures the x-ray absorption at a plurality of transmission paths defined by the x-ray beam during the process. The detector 24 produces a voltage proportional to the intensity of incident x-rays, and the voltage is read and digitized for subsequent processing in a computer. After image data at different gantry angles have been collected, the collected data are processed for reconstruction of a matrix (CT image), which constitutes a depiction of a density function of the bodily section being examined. By considering one or more of such sections, a skilled diagnostician can often diagnose various bodily ailments. In some cases, the one or more sections can also be used to perform treatment planning.

As shown in the figure, the radiation system 10 is used with a marker system 200 that includes a marker block 202 and a camera 204. The camera 204 is coupled to the processor 54, which in accordance with some embodiments, may be a part of the marker system 200. Alternatively, instead of the processor 54, the camera 204 may be coupled to another processor (not shown). Also, in other embodiments, the marker system 200 may not include the camera 204. During use, the marker block 202 is coupled to the patient 16 (e.g., placed on the patient's chest, abdomen, or another body part), and the camera 204 is used to view the marker block 202. The camera 204 transmits image data to the processor 54, which processes the image data to determine a position and/or orientation of the marker block 202.

As shown in the figure, four lasers 60a-60d are positioned adjacent to the system 10. The lasers 60a-60d are configured to generate respective laser beams 62a-62d, which may be used to align the marker block 202 (and therefore, the patient 16) at a desired location. In the illustrated embodiments, lasers 60a, 60b are configured to generate and project laser beams 62a, 62b from opposite sides of the marker block 202, laser 60c is configured to generate and project laser beam 62c from above the marker block 202, and laser 60d is configured to generate and project laser beam 62d downwardly at an angle onto the marker block 202. In other embodiments, the lasers 60 may be configured to project the laser beams 62 from other directions. Each laser 60 may be mounted to any structure, such as a wall, a ceiling, a patient support, or another device. Although four lasers 60 are shown, in other embodiments, more or less than four lasers 60 may be used. For example, in other embodiments, only lasers 60a-60c are used.

Marker System

Figure 2:
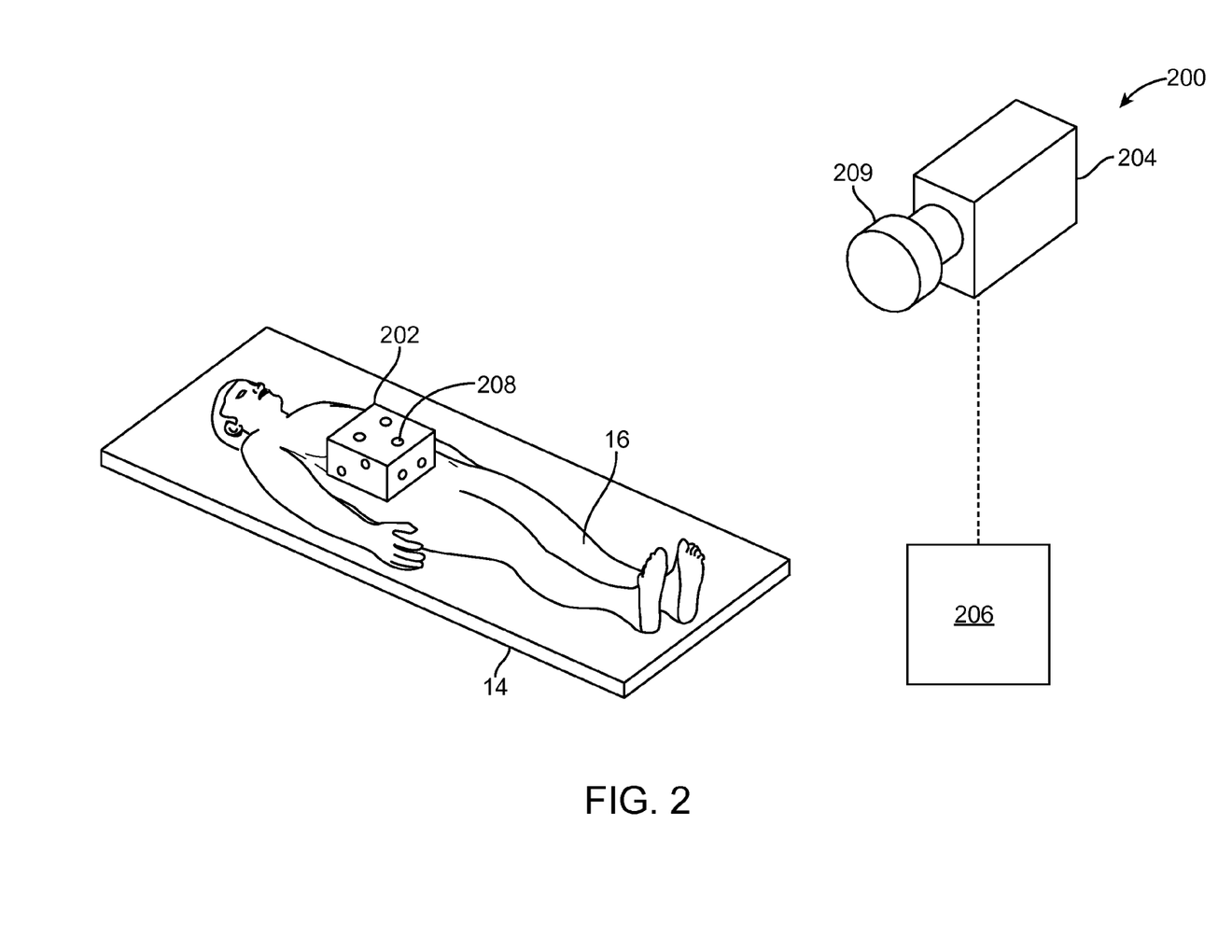
FIG. 2 illustrates a marker system.

FIG. 2 illustrates the marker system 200 of FIG. 1 in accordance with some embodiments. The marker system 200 includes the marker block 202, the camera 204, and a processing unit 206.

The marker block 202 includes a plurality of markers 208. Each marker 208 is configured to emit or reflect light. For example, in some embodiments, each marker 208 may include a LED for emitting light. In some embodiments, each LED is configured to emit infrared light. In other embodiments, each LED is configured to emit UV light. In some cases, each LED is configured to emit light having at least a wavelength of 890 nm. In other embodiments, each LED is configured to emit visible light. Also, in some embodiments, each LED is configured to emit light having a wavelength that is anywhere from 500 nm to 700 nm. In some embodiments, each LED has a half angle that is anywhere between 50° and 70°, and more preferably, anywhere between 55° and 65°, such as 60°. Each LED may be configured to emit light continuously, or in pulses. In other embodiments, instead of LEDs, the light sources may be other types of light bulbs, such as halogen light bulbs, CFL bulbs, incandescent bulbs, etc. Also, in other embodiments, two or more of the markers 208 may share a LED. For example, in other embodiments, a LED may be optically coupled to two or more markers 208 via fiber optics. The LED may be located in the marker block 202, or outside the marker block 202 (remote from the marker block).

In other embodiments, instead of having a light source for emitting light, each marker 208 may include a reflective structure for reflecting light. In such cases, the camera 204 may include a light source for directing light towards the markers 208, so that light can be reflected from the markers 208 for detection by the camera 204.

In further embodiments, each marker 208 may include a material that emits light in certain wavelength(s) in response to light in other wavelength(s) received by the marker 208.

In still further embodiments, each marker 208 may be a device that does not emit or reflect light. For example, in other embodiments, each marker 208 may be any fiducial device that is coupled to the patient.

Figure 3:
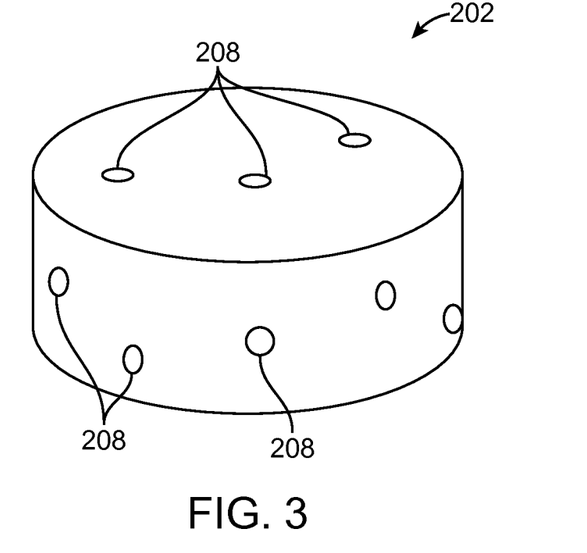
FIG. 3 illustrates a marker block.
Figure 4:
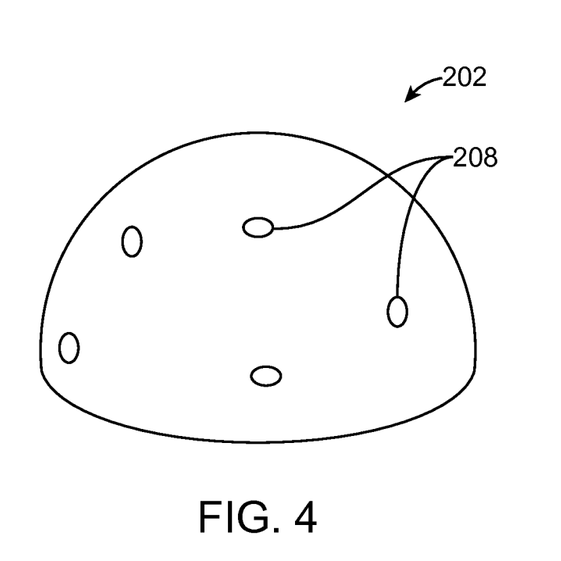
FIG. 4 illustrates another marker block.

In other embodiments, instead of the shape shown in the above example, the marker block 202 can have different shapes. FIG. 3 depicts an embodiment of a marker block 202 having a cylindrical shape with multiple reference locations comprised of markers 208 located on its surface. FIG. 4 depicts an alternate marker block 202 having a hemispherical shape comprised of a plurality of markers 208 attached to its surface.

In other embodiments, the marker block 202 can be formed with shapes to fit particular body parts. For example, molds or casts that match to specific locations on the body can be employed as marker blocks 202. Marker blocks 202 shaped to fit certain areas of the body facilitate the repeatable placement of the marker blocks 202 at particular locations on the patient. Alternatively, the marker blocks 202 can be formed to fit certain fixtures that are attached to a patient's body. For example, a marker block 202 can be formed within indentations and grooves that allow it to be attached to eyeglasses, to a patient's clothing, or to a patient's skin. In yet another embodiment, the fixtures are formed with integral marker block(s) 202 having markers 208 on them.

In further embodiments, the markers 208 may not be secured to a block. For example, in other embodiments, the markers 208 may be individually secured to, or placed on, the portions of the patient 16. In some embodiments, each marker 208 may include a LED or a reflective structure secured to a base, wherein the base has an adhesive for attachment to the patient 16 or to a patient's clothing. In some cases, the adhesive may be made from a biocompatible material to reduce a risk of a skin irritation.

The camera 204 is configured for detecting the markers 208. In some embodiments, the camera 204 may include a filter system 209 that includes one or more filters for reducing ambient light. For example, in some embodiments, the camera 204 may include one or a combination of a notch filter, a high pass filter, a low pass filter, and a bandpass filter. In some cases, the filter(s) is configured to reduce ambient light while allowing at least some of the light from the markers 208 to transmit therethrough. For example, in some embodiments, the camera 204 includes one or more filters for reducing ambient light to a level that corresponds with a noise level of the camera 204 while allowing light from the markers 208 to be imaged by the camera 204. Also, in some cases, the filter(s) may be configured to reduce light being imaged by the camera to a bandwidth anywhere within a range of 10 nm to 100 nm. In further embodiments, the camera 204 may include one or more neutral density filters for reducing ambient light intensity. In still further embodiments, the camera 204 may include one or a combination of a bandpass filter, high pass filter, low pass filter, and neutral density filter. In other embodiments, the camera 204 may not include the filter system 209. For example, in other embodiments, the camera 204 may not include any notch filter, high pass filter, low pass filter, bandpass filter, and/or neutral density filter.

In some embodiments, the camera 204 may be a charge-couple device ("CCD") camera having one or more photoelectric cathodes and one or more CCD devices. A CCD device is a semiconductor device that can store charge in local areas, and upon appropriate control signals, transfers that charge to a readout point. When light photons from the scene to be images are focused on the photoelectric cathodes, electrons are liberated in proportion to light intensity received at the camera. The electrons are captured in charge buckets located within the CCD device. The distribution of captured electrons in the charge buckets represents the image received at the camera. The CCD transfers these electrons to an analog-to-digital converter. The output of the analog-to-digital converter is sent to processing unit 206 to process the video image and to calculate the positions of the markers 208. In other embodiments, the camera 204 may be other types of imaging device. For example, in other embodiments, the camera 204 may be a CMOS camera.

As shown in FIG. 2, the processing unit 206 is communicatively coupled to the camera 204. In some embodiments, the processing unit 206 may be the processor 54 of FIG. 1. In other embodiments, the processing unit 206 may be a component of the processor 54 of FIG. 1, or another component that is communicatively coupled to the processor 54 of FIG. 1. The processing unit 206 may include hardware, software, or combination of both. Also, in some embodiments, the processing unit 206 may include a non-transitory medium for storing data. By means of non-limiting examples, the data may be image data captured by the camera 204, processed image data, and meta data of the image data. The processing unit 206 may be communicatively coupled to the camera 204 via a cable. In other embodiments, the processing unit 206 may be communicatively coupled to the camera via a wireless network.

In operation, the marker block 202 is coupled to the patient 16. The marker block 202 may be placed on the patient 16, and/or may be secured to the patient 16 may a securing mechanism (e.g., adhesive, strap, clip, etc.). The camera 204, which is directed at patient 16, captures and detects the markers 208. The filter system 209 at the camera 204 filters out at least some of the ambient light while allowing light from the markers 208 to be captured by the camera 204. For example, the filter system 209 may reduce ambient light to a level that corresponds with a noise level of the camera 204 while allowing light from the markers 208 to be imaged by the camera 204.

The camera 204 generates video images that show the position of the markers 208 within its video frame. The video images contain mainly images of the LEDs and nothing else (or almost nothing else) in the field of view of the camera 204. The generated video images are sent to processing unit 206 (or another processor) for further processing.

The processing unit 206 (or another processor) receives video images from the camera 204. The processing unit 206 first processes each video image from the camera 204 to identify images of the markers 208 in the image frame. Based on the determined position of the markers 208, and the known relative positions among the markers 208, the processing unit 206 then determines the position (X, Y, Z) and/or orientation ($\theta_x$, $\theta_y$, $\theta_z$) of the marker block 202. In some embodiments, information regarding the location and orientation of the camera 204 is provided to the processing unit 206 to facilitate the computations of the position and/or orientation of the marker block 202.

A possible inefficiency in tracking the markers 208 is that the markers 208 may appear anywhere on the video frame, and all of the image elements of the video frame may have to be examined to determine the location of the markers 208. Thus, in an embodiment, the initial determination of locations for the markers 208 involves an examination of all of the image elements in the video frame. If the video frame comprise 640 by 480 image elements, then all 307200 (640*480) image elements are initially examined to find the location of the markers 208.

For real-time tracking of the markers 208, examining every image element for every video frame to determine the location of the markers 208 in real-time could consume a significant amount of system resources. Thus, in an embodiment, the real-time tracking of the markers 208 can be facilitated by processing a small region of the video frame, referred to herein as "tracking gate", that is placed based on estimation of the locations of the already-identified markers 208 in the video frame. The previously determined location of a marker 208 is used to define an initial search range (i.e., the tracking gate) for that same marker in real-time. The tracking gate is a relatively small portion of the video frame that is centered at the previous location of the marker 208. The tracking gate is expanded only if it does not contain the new location of the marker 208. As an example, consider the situation when the previously determined location of a particular marker is image element (50,50) in a video frame. If the tracking gate is limited to a 50 by 50 area of the video frame, then the tracking gate for this example would comprise the image elements bound within the area defined by the coordinates (25,50), (75,50), (50,25), and (50,75). The other portions of the video frame are searched only if the marker 208 is not found within this tracking gate.

Figure 5:
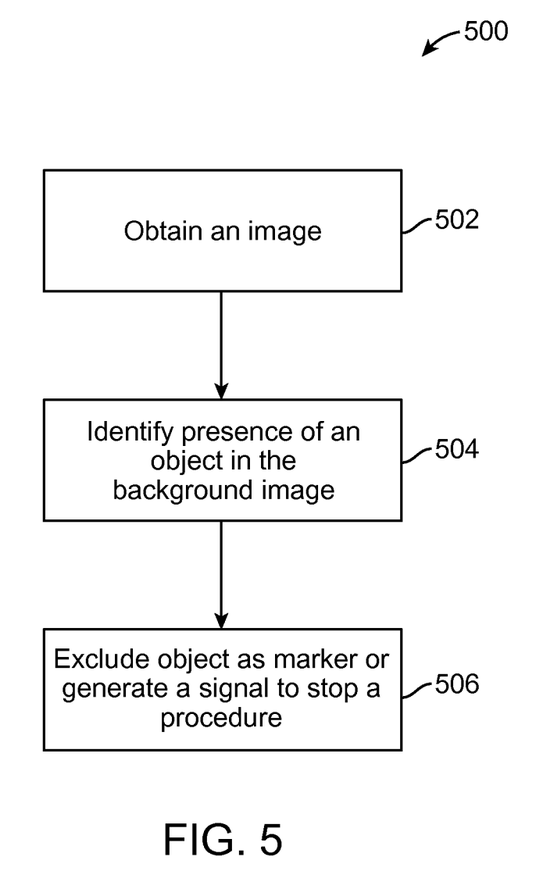
FIG. 5 illustrates a method of processing images.

In some embodiments, an image processing may be performed to ensure that only marker images are being used to determine the position of the marker block 202 or the position or state of the patient. FIG. 5 illustrates an image processing method 500 that may be performed by the processing unit 206, or by another processing unit. First, an image is obtained (item 502). In the illustrated embodiments, the image is generated by the camera 204, and is transmitted to the processing unit 206. Thus, item 502 may be performed by the processing unit 206 receiving the image from the camera 204 in some embodiments. The image received by the processing unit 206 has marker images and a background image (e.g., image of everything else that is not a marker). In other embodiments, the image may be obtained by using the camera 204 to generate the image.

Figure 6:
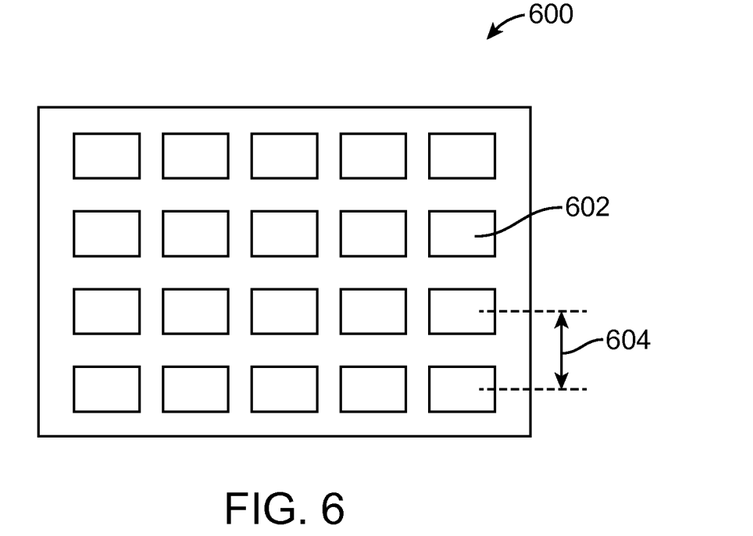
FIG. 6 illustrates a technique of dividing an image into image portions.

Next, presence of an object in the background image is identified (item 504). In some embodiments, item 504 may be performed using the processing unit 206. Various techniques may be employed in different embodiments to detect an object in the background image that is not a marker. In some embodiments, the processing unit 206 may be configured to divide the image into a plurality of image portions arranged in a matrix, for determining whether there is an object in the background image that is not a marker. FIG. 6 illustrates an example of an image 600 that is divided into different image portions 602 (or pixel blocks). Each image portion 602 has a size that may or may not be smaller than a block spacing 604, but the image portions 602 should collectively cover most of the image 600 (e.g., they should be spread throughout the image 600). In some embodiments, each image portion 602 has a width (e.g., along an x-axis) that is the same as a height (e.g., a y-axis). In other embodiments, each image portion 602 has a width that is different from its height.

The size for one or more of the image portions 602 may be set manually. Alternatively, the processing unit 206 may be configured to set the size of the image portions 602 automatically using an algorithm. In one implementation, the processing unit 206 may employ an algorithm for automatically set the size of the image portions 602. The processing unit 206 may take an initial image frame and determine a "local" standard deviation of pixel values, e.g., a standard deviation over a small region. This will provide a measure of the statistical noise in the image. In some embodiments, such may be accomplished by measuring the standard deviation of pixel values over a block (e.g., 5×5 size), and computing $\mu_o$, the average of all such standard deviations over all such blocks over the image. Such technique may allow the processing unit 206 to determine the variation due to noise but ignoring the effects of large scale variations in grayscale value. In some embodiments, the processing unit 206 may be configured to determine the standard deviation of the entire image. During a detection phase, the processing unit 206 may define a set of block sizes N1, N2, ... Nn, where n is 2 or 3. The processing unit 206 performs the previously described basic detection algorithm on each image frame n times, using each of the block sizes in the set. For a given block size Ni, the standard deviation of block averages may be the same as the standard error of the mean (SEM) of grayscale values: $SEM=\mu_o/Ni$. Then the threshold T for that block size should be set to some multiple of the SEM (e.g., T=3×SEM+offset), with the rationale that it should be statistically unlikely for a value in the block value map to differ by more than T from the average value in the map. Therefore, one may conclude that such a block value is not due to noise. The smallest block size may be set as default to be 2 or 3 pixels in size, and the largest may be set so that the SEM value is small (e.g., 0.3). In other embodiments, the processing unit 206 may compute a standard deviation over the whole image (instead of over a portion of the image).

After the image portions 602 are determined, the processing unit 206 then determines a mean or median value of pixel values in each of the image portions 602 in the image. The image may be the entire image frame, or a subset or a portion within the image frame. Next, the processing unit 206 determines a histogram using the determined mean or median values. The processing unit 206 then determines if any of the mean or median values exceeds a peak value of the histogram by more than a specified threshold. If so, then the processing unit 206 may determine that there is an object in the background that is not a marker.

Returning to FIG. 5, if the processing unit 206 determines that there is an object in the background that is not a marker, the processing unit 206 then excludes the object as a marker for future processing in a procedure and/or stops the procedure (item 506). For example, in some embodiments, the procedure may be a tracking of a tissue, treatment of a tissue, or a gating of a medical process (e.g., gating a delivery of a radiation or proton beam). In such cases, when the presence of the object has been identified in the background image, the processing unit 206 may generate a signal to stop the procedure, and then removes the object from the camera image so that the object is excluded as a marker in the procedure. After the object has been excluded as a marker, the processing unit 206 may generate another signal to re-start the procedure. Alternatively, the procedure may remain stopped until an input (e.g., an instruction to re-start the procedure) is received from a user. In some embodiments, the procedure is stopped until a decision based on tracking is made (e.g., by the processing unit 206, by another processing unit, or by a user). For example, the decision may be whether to continue with treatment, whether to operate a component of a treatment system, such as whether to rotate a radiation source, to move a patient support, to operate a collimator, etc, or other decisions related to a medical procedure.

In some embodiments, if none of the mean or median values exceeds the peak value of the histogram by more than the specified threshold, then processing unit 206 may determine that there is no "non-marker" object in the background.

The method 500 is advantageous because it allows detection of pixels in the image (other than the designated foreground pixels, such as pixels of marker images) that are visibly brighter than the average background. Thus, all objects that are distinguishable from noise, and that are not the markers intended to be detected, can be detected.

Figure 7:
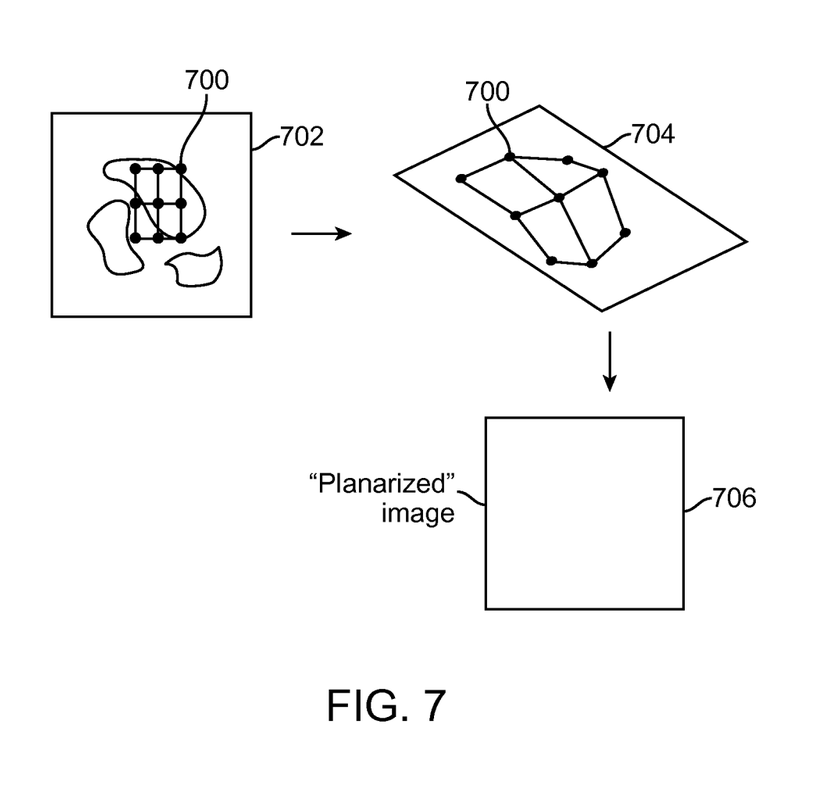
FIG. 7 illustrates a technique of flattening an image in grayscale.

In some embodiments, the method 500 may optionally also include flattening the image in greyscale so that gradient variation across the image is reduced. This feature may be desirable because in some camera images, there may be a gradient in grayscale over the whole image which may tend to create false positives in the background object detection. In such cases, it may be beneficial to planarize the image (e.g., flatten it in grayscale) so that the gradient variation is reduced, or as small as possible. In one implementation, the processing unit 206 is configured for sampling a set of points in the image. For example, the processing unit 206 may take a subsample set of points, such as an 3×3 points grid 700, from the image 702 (FIG. 7). Each point may have a value that is an average of a 3×3 set of pixels centered about the point location. In other example, the grid 700 may be a 8×12 grid, with each point being a value that is an average of a 3×3 set of pixels centered about the point location. The processing unit 206 then generates an uniform gradient image 704 with uniform grayscale gradient which is the best-fit to the sampled set of points. One way to think of this is to treat the grayscale as a third dimension, and to represent the grid of points as a 3D plot in which the grayscale value at each point represents the "height" of the point at each x, y position. The uniform gradient image may be represented by a plane 704 which is the best fit to that 3D grid 700 (e.g., by least-square fitting, etc.). The processing unit 206 then subtracts the uniform gradient image 704 from the received image 702 to generate an output image 706 (a more "planarized" image in terms of grayscale). The output image 706 may then be processed to identify a possible object in the background (in item 504). In some embodiments, the output image 706 may be used as the image in item 502. In such cases, item 502 may be performed by the processing unit 206 obtaining the output image 706 (e.g., by receiving the output image from another processing unit, or by determining the output image 706 using the above described flattening procedure).

Also, in some embodiments, a user may specify a set of foreground pixels, which are not to be treated as background, and are to be excluded from detection. In such cases, the algorithm for implementing the method 500 may handle this by setting the designated foreground pixels to zero grayscale value.

In some embodiments, the method 500 may be performed by the processing unit 206 for every image frame received from the camera 204. For example, in some embodiments, the method 500 may be performed by the processing unit 206 fast enough so that it can be performed on every image frame from the camera video stream (e.g., with a 30 Hz frame rate or faster). In other embodiments, the method 500 may be performed by the processing unit 206 for every Nth image received from the camera 204. For example, in some embodiments, the processing unit 206 is configured to receive a sequence of images from the camera 204, and is configured to perform the method 500 on a subset of the sequence of images (e.g., every 5th image).

In other embodiments, the processing unit 206 may be configured to select only a portion of the image area as test block(s). The portion may change from frame to frame to get total coverage over the course of several frames. For example, an image frame may be divided into 4 portions (4 quadrants). The processing unit 206 may process the first quadrant for a first image, a second quadrant for a second image, a third quadrant for a third image, and a fourth quadrant for the fourth image. In this way, every portion of the entire image area is examined at least once for background objects over the course of several frames, but the processing unit 206 does not have to process every pixel of the image on any one given frame.

In some embodiments, the determined position and/or orientation of the marker block 202 can then be used to position the patient 16 at desired position and/or orientation. For example, the determined position of the marker block 202 may be compared with a prescribed position of the marker block 202. In such cases, if the determined position of the marker block 202 matches with the prescribed position, the patient 16 is then considered to be correctly positioned. On the other hand, if the determined position of the marker block 202 does not match the prescribed position, the patient 16 is then positioned (e.g., by moving the patient support 14) until the marker block 202 position matches with the prescribed position.

In other embodiments, the determined position and/or orientation of the marker block 202 can be used to determine the position of at least a portion of the patient 16. In such cases, the relative spatial relationship between the marker block 202 and the patient 16 is known or predetermined. As such, once the marker block 202 position is determined, the position of the portion of the patient 16 can then be determined (e.g., via the processing unit 206) based on the relative spatial relationship between the marker block 202 and the patient 16. In some embodiments, by continuously determining the position of the portion of the patient 16 in real time, the portion of the patient 16 can be tracked in real time. The tracked position of the patient 16 may be used to gate an application of radiation provided by the system 10. In further embodiments, the tracked position of the patient 16 may be used to perform tracking of a target region while an intensity modulated radiation therapy (IMRT) is being performed. In IMRT, a multileaf collimator is operated such that a first portion of the target region receives more radiation than a second portion of the target region during a treatment session.

In further embodiments, the determined position of the marker block 202 can be used to determine a level of activity accomplished by the patient 16. For example, if the marker block 202 is placed on the patient's chest, then the determined position of the marker block 202 can be used to determine a level of breathing performed by the patient 16. In some cases, by determining a plurality of positions of the marker block 202 over a period of time, the processing unit 206 can be configured to obtain a plurality of amplitude points that correspond to the patient's levels of breathing at various time points in that period. The determined amplitude points may be used to gate an execution of a procedure, such as, to gate an application of a treatment radiation to the patient 16 for treatment, or to gate an application of an imaging radiation to the patient 16 for imaging purpose. In other embodiments, the determined positions of the marker block 202 (or the amplitude points) may be used to gate a binning of image data, either in real time, or after the image data has been obtained.

In further embodiments, the amplitude points may be used to perform tracking of a target region while IMRT is being performed. Since the amplitude values are determined using only the marker images without any object image from the background image, the gating of the medical procedure is based on only the marker images, and any object in the background image is excluded for the act of gating.

Figure 8:
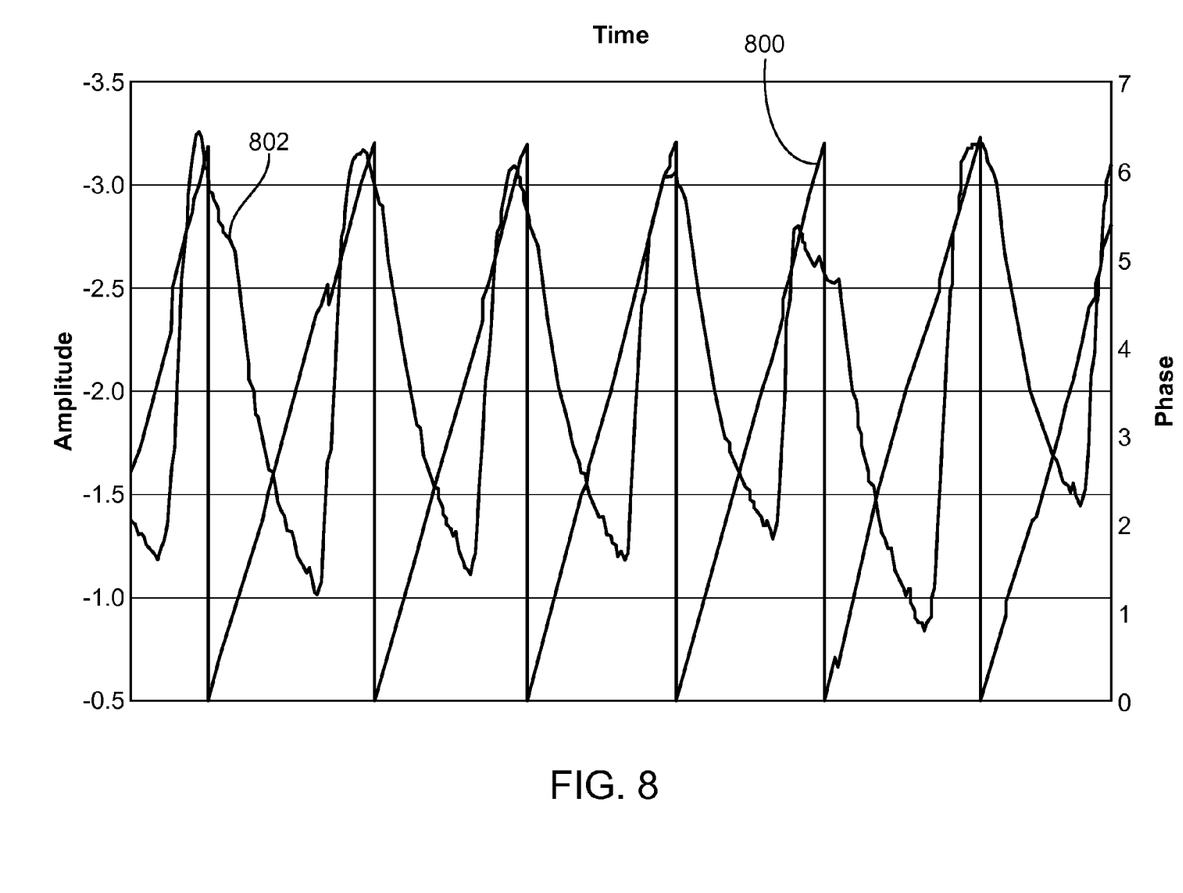
FIG. 8 illustrates an amplitude diagram and a corresponding phase diagram.

In further embodiments, by determining a plurality of positions of the marker block 202 over a period of time, the processing unit 206 can be configured to obtain a plurality of phase points that correspond to different levels of completeness of a breathing cycle at various time points. For example, a phase value may have a value from 0° to 360°, with 0° representing a beginning of a respiratory cycle, and 360° representing an end of the respiratory cycle. FIG. 8 illustrates an example of a phase diagram 800 that is aligned with a corresponding amplitude/position diagram 802. Amplitude diagram 802 includes positional points of the marker block 202 determined using embodiments of the technique described herein. Each point in the amplitude diagram 802 represents a position of the marker block 202 or a bodily part at a certain point in time. In the illustrated example, a phase value of 0° (and 360°) represents a peak of an inhale state, and the phase value varies linearly between 0° and 360° in a physiological cycle. As shown in the diagram, for each point in the amplitude diagram 802 at certain point in time, a corresponding phase value at the same point in time may be obtained. Thus, for each breathing amplitude, the processing unit 206 can determine the corresponding phase of the respiratory cycle.

In some embodiments, the determined phase values may be used to gate an execution of a procedure, such as, to gate an application of a treatment radiation to the patient 16 for treatment, or to gate an application of an imaging radiation to the patient 16 for imaging purpose. In further embodiments, the phase values may be used to perform tracking of a target region while IMRT is being performed. Since the phase values are determined using only the marker images without any object image from the background image, the gating of the medical procedure is based on only the marker images, and any object in the background image is excluded for the act of gating.

In other embodiments, the determined phase values may be used to gate a binning of image data, either in real time while the image data is being obtained, or after the image data has been obtained. For example, in a 4D-CT imaging session, the marker system 200 may be used to determine the positions of the marker block 202 representing different breathing amplitudes of the patient 16, while a CT machine generates different projection images of the patient 16 at different respective gantry angles. The positions of the marker block 202 may be used to determine breathing phases for association with different projection images. For example, different projection images generated at different gantry angles but belonging to a same phase range (phase bin) may be associated together. The associated projection images may then be used to construct a volumetric CT image for that particular phase bin. Also, in some embodiments, different volumetric CT images for different phase bins may be constructed (e.g., using the processing unit 206 or another processor), and the sequence of volumetric CT images may be displayed in a video.

One advantage to using the marker block 202 is that with a-priori knowledge of the relative positions of the markers 208 on the marker block 202, it is possible to determine all six degrees of freedom (X, Y, Z, $\theta_x$, $\theta_y$, $\theta_z$) of the marker block 202 from a single camera view. In other words, only a single camera is required to derive the absolute coordinates of a marker block 202. This results because the relative positioning between the markers 208 on the marker block 202 are known, and the absolute coordinates and viewing orientation of the camera 204 are also known. The detected image of the marker block 202 by the camera 204 indicates the positioning of the visible reference locations 208 relative to the camera's viewing orientation. Because the actual relative positions between the markers 208 are known, the detected relative coordinates of the markers 208 from the camera image can be used to derive the absolute coordinate of the marker block 202. The marker block 202 is also advantageous because its configuration allows the camera 204 to detect the markers 208 accurately.

Although the marker system 200 has been described as having one camera 204, in other embodiments, the marker system 200 can have more than one camera. For example, in alternative embodiments, the marker system 200 may include two cameras which detect the markers 208. In such cases, the processor 54/206 receives image data from the two cameras, and determines a position of the marker block 202 using triangulation technique, as is known in the art. Also, in other embodiments, instead of a camera, the marker system 200 may include other types of optical devices that are capable of detecting the markers 208.

Also, it should be understood by those skilled in the art that the marker system 200 can be used with different systems in different embodiments. For example, the radiation system 10 needs not be a treatment device, and may be any machine that is capable of generating a radiation beam. In some embodiments, the radiation system 10 may be any types of imaging or optical devices, such as a CT imaging device (e.g., a cone beam CT device), a laminar tomography machine, a MRI machine, a C-arm based x-ray imaging machine, a three dimensional angiography machine, or a PET machine. Also, in other embodiments, any of the marker systems 200 and/or methods described herein can be used with non-imaging devices, such as a positioner or a treatment machine that has no imaging capability. In further embodiments, any of the marker systems 200 and/or methods described herein can be used with a machine that has a plurality of radiation sources. For example, the machine can have a first radiation source for delivering diagnostic radiation (e.g., radiation having an energy level in the kilo-electron-volt range), and a second radiation source for delivering treatment radiation (e.g., radiation having an energy level in the mega-electron-volt range). As another example, the machine can also have a plurality of diagnostic radiation sources and/or one or more treatment radiation sources.

Also, in other embodiments, instead of using markers that emit light and camera that detects light, other types of energy/signal emitting devices and signal detectors may be used. For example, in other embodiments, electromagnetic field beacons may be used as markers that emit electromagnetic signals. In one implementation, Calypso beacons available from Varian Medical Systems, Inc. may be placed on a marker block. The beacons provide electromagnetic emission and the positions of the beacons may be detected by an electromagnetic detector array that is exterior to the patient. In some embodiments, the beacons may be excited by an external source. In further embodiments, instead of light or electromagnetic signal, the markers may emit other types of signal.

Computer System Architecture

Figure 9:
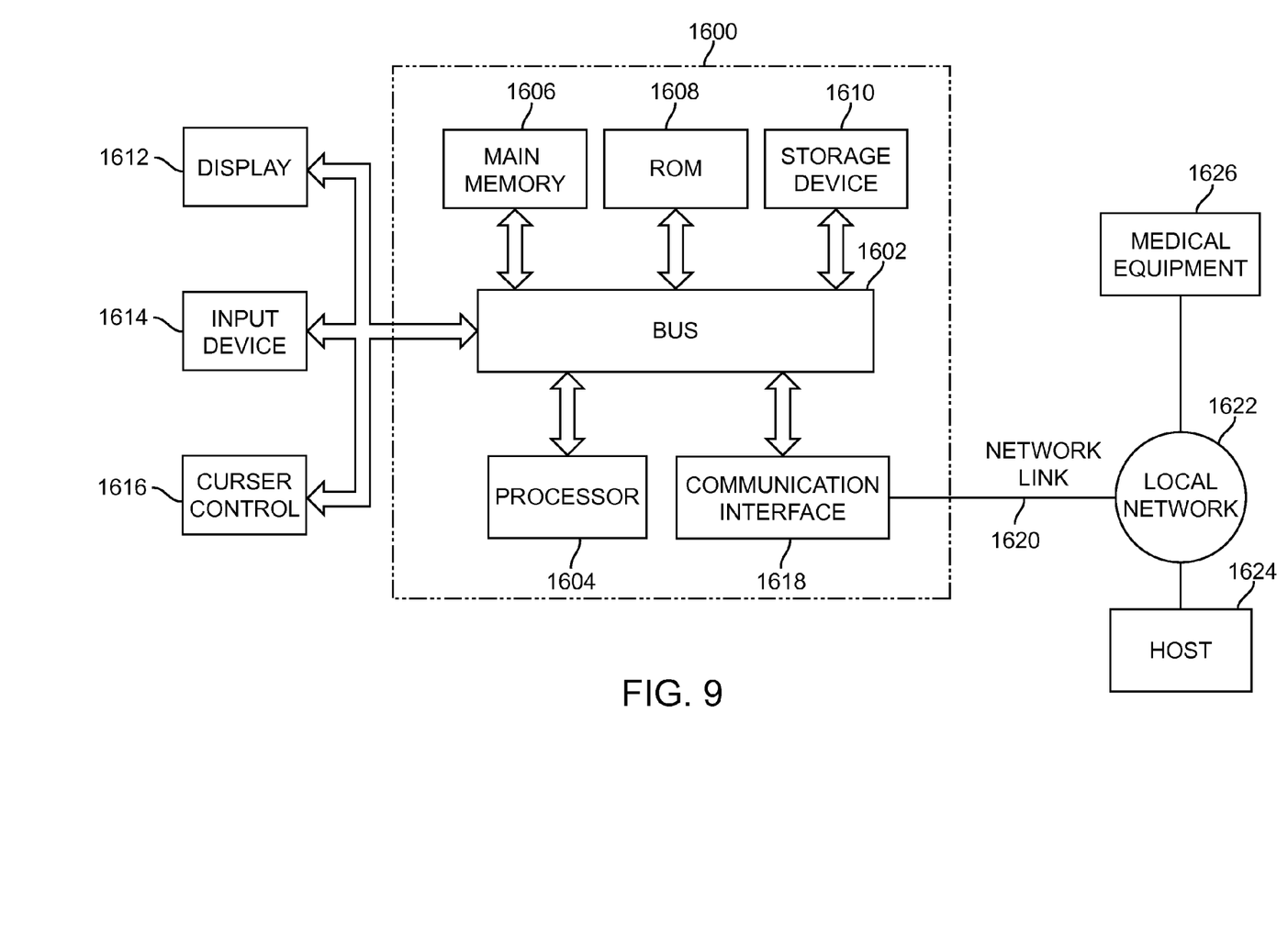
FIG. 9 illustrates a computer system.

FIG. 9 is a block diagram illustrating an embodiment of a computer system 1600 that can be used to implement various embodiments described herein. Computer system 1600 includes a bus 1602 or other communication mechanism for communicating information, and a processor 1604 coupled with the bus 1602 for processing information. The processor 1604 may be an example of the processor 54 of FIG. 1, an example of the processing unit 206 of FIG. 2, or an example of any processor described herein. The computer system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The computer system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The computer system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the computer system 1600 can be used to perform various functions described herein. According to some embodiments, such use is provided by computer system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. Volatile media includes dynamic memory, such as the main memory 1606. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the computer system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The computer system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the computer system 1600, are exemplary forms of carrier waves transporting the information. The computer system 1600 can send messages and receive data, including program code, through the network(s), the network link 1620, and the communication interface 1618.

It should be noted that as used in this specification, the term "image" may refer to an image that is displayed (e.g., in a screen), or an image that is stored in a non-transitory medium.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The invention claimed is:

1. An image processing method, comprising:
   obtaining an image, the image having marker images and a background image;
   identifying presence of an object in the background image using a processor; and
   providing a signal for stopping a procedure if the presence of the object is identified;
   wherein the method further comprises reducing gradient variation across the image by (1) sampling a set of points in the image, (2) generating a gradient image with grayscale gradient that corresponds with the sampled set of points, and (3) subtracting the gradient image from the image.

2. The method of claim 1, wherein the act of identifying the presence of the object in the background comprises:
   dividing the image into a plurality of image portions arranged in a matrix; and
   determines a mean or median value of pixel values in each of the image portions.

3. The method of claim 2, wherein the act of identifying the presence of the object in the background further comprises determining a histogram using the determined mean or median values.

4. The method of claim 3, wherein the act of identifying the presence of the object further comprises determining if any of the mean or median values exceeds a peak value of the histogram by more than a specified threshold.

5. The method of claim 2, further comprising setting a size for one or more of the image portions.

6. The method of claim 5, wherein the size is set manually.

7. The method of claim 5, wherein the size is set automatically using the processor.

8. The method of claim 1, wherein
   the gradient image comprises an uniform gradient image with uniform grayscale gradient which is the best-fit to the sampled set of points.

9. The method of claim 1, further comprising excluding the object as a marker.

10. The method of claim 1, wherein the act of receiving an image comprises receiving a sequence of images that includes the image, and the act of identifying the presence of the object is performed on a subset of the sequence of images.

11. An image processing apparatus, comprising:
    a processor configured for:
    obtaining an image, the image having marker images and a background image;
    identifying presence of an object in the background image; and
    providing a signal for stopping a procedure if the presence of the object is identified;
    wherein the processor is further configured for reducing gradient variation across the image by (1) sampling a set of points in the image, (2) generating a gradient image with grayscale gradient that corresponds with the sampled set of points, and (3) subtracting the gradient image from the image.

12. The apparatus of claim 11, wherein the processor is configured for:
    dividing the image into a plurality of image portions arranged in a matrix; and
    determines a mean or median value of pixel values in each of the image portions.

13. The apparatus of claim 12, wherein the processor is configured for determining a histogram using the determined mean or median values.

14. The apparatus of claim 13, wherein the processor is configured for determining if any of the mean or median values exceeds a peak value of the histogram by more than a specified threshold.

15. The apparatus of claim 12, wherein the processor is configured to obtain a size for one or more of the image portions.

16. The apparatus of claim 15, wherein the processor is configured to obtain the size by receiving an input from a user that represents the size.

17. The apparatus of claim 15, wherein the processor is configured to obtain the size by determining the size using an algorithm.

18. The apparatus of claim 11, wherein
the gradient image comprises an uniform gradient image with uniform grayscale gradient which is the best-fit to the sampled set of points.

19. The apparatus of claim 11, wherein the processor is further configured to exclude the object as a marker.

20. The apparatus of claim 11, wherein the processor is configured to receive a sequence of images that includes the image, and the processor is configured to perform the act of identifying the presence of the object on a subset of the sequence of images.

21. A computer product having a non-transitory medium storing a set of instructions, an execution of which causes an image processing method to be performed, the method comprising:
receiving an image, the image having marker images and a background image;
identifying presence of an object in the background image; and
providing a signal for stopping a procedure if the presence of the object is identified;
wherein the method further comprises reducing gradient variation across the image by (1) sampling a set of points in the image, (2) generating a gradient image with grayscale gradient that corresponds with the sampled set of points, and (3) subtracting the gradient image from the image.

* * * * *